(12) United States Patent
Mizuta et al.

(10) Patent No.: US 10,278,669 B2
(45) Date of Patent: May 7, 2019

(54) NUCLEAR MEDICAL DIAGNOSIS APPARATUS AND METHOD FOR ROUTINE MAINTENANCE AND INSPECTION OF NUCLEAR MEDICAL DIAGNOSIS APPARATUS

(71) Applicant: Shimadzu Corporation, Kyoto (JP)

(72) Inventors: Tetsuro Mizuta, Kyoto (JP); Atsushi Ohtani, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 16/015,569

(22) Filed: Jun. 22, 2018

(65) Prior Publication Data

US 2018/0368802 A1 Dec. 27, 2018

(30) Foreign Application Priority Data

Jun. 23, 2017 (JP) .................. 2017-123400

(51) Int. Cl.
  *A61B 6/00* (2006.01)
  *A61B 6/03* (2006.01)
  *G01T 7/00* (2006.01)
  *G01T 1/29* (2006.01)
  *G06T 11/00* (2006.01)

(52) U.S. Cl.
  CPC .............. *A61B 6/585* (2013.01); *A61B 6/037* (2013.01); *A61B 6/4266* (2013.01); *A61B 6/54* (2013.01); *G01T 1/2985* (2013.01); *G01T 7/005* (2013.01); *G06T 11/005* (2013.01); *G06T 2211/40* (2013.01)

(58) Field of Classification Search
  CPC ... A61B 2576/00; A61B 5/7225; A61B 6/585; A61B 6/037; G06T 11/005; G01T 7/005
  See application file for complete search history.

(56) References Cited

U.S. PATENT DOCUMENTS

| | | | |
|---|---|---|---|
| 2009/0314933 A1* | 12/2009 | Breuer ................ | A61B 6/037 250/252.1 |
| 2014/0093150 A1* | 4/2014 | Zalev ................... | G06T 7/0012 382/131 |
| 2018/0140725 A1* | 5/2018 | Perez-Medina ....... | C07B 59/008 |

OTHER PUBLICATIONS

"Foundations of PET and PET/CT inspection technology", by Nuclear Medicine Subcommittee, Japanese Society of Radiological Technology, Feb. 23, 2009, p. 21.

* cited by examiner

*Primary Examiner* — Yara B Green
(74) *Attorney, Agent, or Firm* — Maier & Maier, PLLC

(57) ABSTRACT

This nuclear medical diagnosis apparatus acquires a normalization factor based on reference data of a reference object to be measured, acquires a mutual calibration factor using at least a part of the reference data, and calculates radioactive concentration of the reference object to be measured.

10 Claims, 4 Drawing Sheets

FIRST EMBODIMENT (SECOND EMBODIMENT)

*FIG.1*
FIRST EMBODIMENT (SECOND EMBODIMENT)

*FIG.2*
FIRST EMBODIMENT (SECOND EMBODIMENT)

FIG.3
FIRST EMBODIMENT

FIG.4
FIRST EMBODIMENT

FIG.5
SECOND EMBODIMENT

FIG.6
SECOND EMBODIMENT

FIG.7

MODIFICATION OF EMBODIMENT 1

NUCLEAR MEDICAL DIAGNOSIS APPARATUS AND METHOD FOR ROUTINE MAINTENANCE AND INSPECTION OF NUCLEAR MEDICAL DIAGNOSIS APPARATUS

CROSS-REFERENCE TO RELATED APPLICATIONS

The priority application number JP2017-123400, NUCLEAR MEDICAL DIAGNOSIS APPARATUS AND METHOD FOR ROUTINE MAINTENANCE AND INSPECTION OF NUCLEAR MEDICAL DIAGNOSIS APPARATUS, Jun. 23, 2017, Tetsuro Mizuta and Atsushi Ohtani, upon which this patent application is based are hereby incorporated by reference.

FIELD

The present invention relates to a nuclear medical diagnosis apparatus, and particularly relates to a nuclear medical diagnosis apparatus having functions of normalization of deviations of detection efficiencies among a plurality of detectors, mutual calibration to a measured value of a radiation detector, and confirmation of a quantitative value of radioactive concentration, and a method for routine maintenance and inspection of the nuclear medical diagnosis apparatus.

BACKGROUND

Conventionally, a nuclear medical diagnosis apparatus for normalizing deviations of detection efficiencies among a plurality of detectors and a method for routine maintenance and inspection of the nuclear medical diagnosis apparatus have been known. For example, such a nuclear medical diagnosis apparatus and method for routine maintenance and inspection of the nuclear medical diagnosis apparatus are disclosed on p. 21 of "Foundations of PET and PET/CT inspection technology" written by Nuclear Medicine Subcommittee and published by Japanese Society of Radiological Technology on Feb. 23, 2009.

A positron emission tomography (PET) device (nuclear medical diagnosis apparatus) described on p. 21 of "Foundations of PET and PET/CT inspection technology" written by Nuclear Medicine Subcommittee and published by Japanese Society of Radiological Technology on Feb. 23, 2009 includes a plurality of detectors that detects annihilation radiation. In addition, in routine maintenance and inspection of the device, the PET device is configured to perform normalization scan for normalizing a detection deviation between a plurality of detector pairs using a reference object to be measured adjusted to predetermined radioactive concentration and cross-calibration scan for calibrating a pixel value obtained by image reconstruction of measured data of PET to a measured value of a radiation detector such as Curie meter, a well counter, etc. In addition, in general, the PET device is urged to reconstruct an image by applying a normalization factor obtained in normalization scan and a mutual calibration factor obtained in cross-calibration scan, and perform quantitative value confirmation to confirm that a pixel value of the obtained image reproduces radioactive concentration of the reference object to be measured. In general, data acquisition is separately performed in each of normalization scan, cross-calibration scan, and quantitative value confirmation, and each of the above processes is performed using separately obtained data.

However, in the conventional PET device (nuclear medical diagnosis apparatus) described on p. 21 of "Foundations of PET and PET/CT inspection technology" written by Nuclear Medicine Subcommittee and published by Japanese Society of Radiological Technology on Feb. 23, 2009, data acquisition is separately performed in each of processes of normalization scan, cross-calibration scan, and quantitative value confirmation. Thus, it is necessary to input a parameter used for data acquisition in each process or create a reference object to be measured, which causes a problem that a workload of a user increases.

SUMMARY

The invention has been made to solve the above-mentioned problem, and an object of the invention is to provide a nuclear medical diagnosis apparatus capable of reducing a workload of a user in routine maintenance and inspection of the apparatus, and a method for routine maintenance and inspection of the nuclear medical diagnosis apparatus.

To achieve the above object, a nuclear medical diagnosis apparatus according to a first aspect of the invention includes a plurality of detectors that detects annihilation radiation emitted from a reference object to be measured, a data acquisition unit that acquires reference data of the reference object to be measured based on a result of detecting, by the plurality of detectors, the annihilation radiation emitted from the reference object to be measured, a normalization unit that acquires a normalization factor for normalizing deviations of detection efficiencies among the plurality of detectors based on the reference data, a calibration unit that applies the normalization factor to at least a part of the reference data used for acquisition of the normalization factor to acquire a mutual calibration factor for calibrating a pixel value of a reconstructed image of the reference object to be measured to radioactive concentration of the reference object to be measured, and a quantitative value confirmation unit that compares radioactive concentration of the reference object to be measured calculated from a pixel value of an image of the reference object to be measured acquired by applying each of the normalization factor and the mutual calibration factor to at least a part of the reference data used for acquisition of the normalization factor with a quantitative value of the radioactive concentration of the reference object to be measured.

In the nuclear medical diagnosis apparatus according to the first aspect of the invention, as described above, when the normalization factor is acquired based on the reference data, the mutual calibration factor is acquired using at least a part of the reference data used for acquisition of the normalization factor, and the radioactive concentration of the reference object to be measured is calculated, it is possible to acquire the normalization factor, acquire the mutual calibration factor, and calculate the radioactive concentration of the reference object to be measured using common data. In this way, when compared to a case in which data is separately acquired for each of acquisition of the normalization factor, acquisition of the mutual calibration factor, and calculation of the radioactive concentration of the reference object to be measured, it is possible to reduce the number of times of input of a parameter necessary for data acquisition, creation of the reference object to be measured, etc. in each process of routine maintenance and inspection of the apparatus, and thus it is possible to reduce a workload of a user. In addition, it is possible to shorten working hours when compared to a case in which data is separately acquired.

In addition, in a conventional nuclear medical diagnosis apparatus, the reference object to be measured may be created only for acquisition of the mutual calibration factor and quantitative value confirmation of the radioactive concentration of the reference object to be measured. When compared to this case, it is possible to omit an effort to create the reference object to be measured, and thus it is possible to effectively reduce the workload of the user. In addition, since the reference object to be measured is created only once, it is possible to prevent occurrence of a measurement error due to a deviation of radioactive concentration of the created reference object to be measured.

In the nuclear medical diagnosis apparatus according to the first aspect, preferably, the data acquisition unit is configured to acquire reference data by performing measurement once. In this way, when compared to a case in which data is acquired a plurality of times, it is possible to further reduce the workload of the user. In addition, since measurement is performed only once, the number of parameter inputs required each time measurement is performed can be reduced to once. As a result, occurrence of an erroneous input of a parameter can be suppressed.

In the nuclear medical diagnosis apparatus according to the first aspect, preferably, the calibration unit designates calibration data used for image reconstruction corresponding to a first area which is a part of the reference data and acquires the mutual calibration factor by applying the normalization factor to the calibration data to reconstruct the image, and the quantitative value confirmation unit designates confirmation data corresponding to a second area which is a part of the reference data and calculates radioactive concentration of the reference object to be measured by applying each of the normalization factor and the mutual calibration factor to the confirmation data. According to such a configuration, it is possible to arbitrarily designate the calibration data and the confirmation data from the reference data. As a result, it is possible to easily acquire data suitable for a condition of radiation intensity, etc. required by the user.

In this case, preferably, the calibration unit is configured to designate pieces of calibration data corresponding to a plurality of different first areas in the reference data, respectively, to acquire a plurality of mutual calibration factors corresponding to the plurality of pieces of calibration data, respectively. According to such a configuration, it is possible to easily acquire and evaluate the mutual calibration factor corresponding to the radiation intensity of the radiation source by designating the plurality of pieces of calibration data from one piece of reference data. As a result, it is possible to effectively reduce the workload of the user when compared to a case in which the calibration data is separately acquired a plurality of times to acquire and evaluate the mutual calibration factor corresponding to the radiation intensity of the radiation source.

Here, when the radioactive concentration of the radiation source is high, the number of annihilation radiation rays emitted from the radiation source is relatively large, and thus a possibility of occurrence of counting loss of annihilation radiation by the detector increases. Therefore, when a counting loss correction factor is acquired based on a mutual calibration factor acquired after radioactive concentration of the radiation source decreases as in the conventional nuclear medical diagnosis apparatus, counting loss may not be accurately corrected in an area in which the radioactive concentration of the radiation source is high. For this reason, the conventional nuclear medical diagnosis apparatus separately requires a process for correcting counting loss apart from a cross-calibration process of acquiring a mutual calibration factor.

On the contrary, in the invention, since the mutual calibration factor corresponding to the radiation intensity of the radiation source may be acquired by acquiring the mutual calibration factor corresponding to each of the plurality of different first areas, it is possible to acquire the counting loss correction factor corresponding to the radiation intensity of the radiation source based on each acquired mutual calibration factor. That is, when the mutual calibration factor corresponding to the radiation intensity of the radiation source is acquired, the counting loss correction factor corresponding to the radiation intensity of the radiation source may be acquired at the same time, and thus a process for correcting the counting loss may not be separately performed. In this way, it is possible to suppress an increase in maintenance workload.

In the nuclear medical diagnosis apparatus in which the quantitative value confirmation unit designates the confirmation data corresponding to the second area, preferably, the quantitative value confirmation unit is configured to designate pieces of confirmation data corresponding to a plurality of different second areas in the reference data, respectively, to calculate radioactive concentrations of the reference object to be measured corresponding to the plurality of pieces of confirmation data, respectively. According to such a configuration, it is possible to easily perform quantitative value confirmation for the radioactive concentration of the reference object to be measured corresponding to the radiation intensity of the radiation source by designating the plurality of pieces of confirmation data from the one piece of reference data. As a result, it is possible to effectively reduce the workload of the user when compared to a case in which confirmation data is separately acquired a plurality of times to perform quantitative value confirmation for the radioactive concentration of the reference object to be measured corresponding to the radiation intensity of the radiation source.

In the nuclear medical diagnosis apparatus according to the first aspect, preferably, the normalization unit is configured to determine that a normalization factor acquired this time is valid when a difference between the normalization factor acquired this time and a normalization factor acquired at a previous time is within a first ratio of the normalization factor acquired at the previous time, the calibration unit is configured to determine that a mutual calibration factor acquired this time is valid when a difference between the mutual calibration factor acquired this time and a mutual calibration factor acquired at a previous time is within a second ratio of the mutual calibration factor acquired at the previous time, and the quantitative value confirmation unit is configured to determine that radioactive concentration of the reference object to be measured calculated this time is valid when a difference between the calculated radioactive concentration of the reference object to be measured and a quantitative value of radioactive concentration of the reference object to be measured acquired in advance is within a third ratio of the quantitative value of the radioactive concentration of the reference object to be measured acquired in advance. Here, in the conventional nuclear medical diagnosis apparatus, in general, the user determines validity of each of the normalization factor, the mutual calibration factor, and the radioactive concentration of the reference object to be measured. Therefore, when the normalization unit, the calibration unit, and the quantitative value confirmation unit determine validities of the normalization factor, the mutual calibration factor, and the radioactive concentration of the reference object to be measured, respectively, it is possible to further reduce the workload of the user. In addition, when compared to a case in which the user determines validities of the normalization factor, the mutual calibration factor, and the radioactive concentration of the reference object to be measured, it is possible to suppress occurrence of an artificial deviation in a determination result.

In this case, preferably, the normalization unit registers the normalization factor when it is determined that the normalization factor is valid, the calibration unit registers the mutual calibration factor when it is determined that the mutual calibration factor is valid, and the quantitative value confirmation unit registers the calculated radioactive concentration of the reference object to be measured when it is determined that the calculated radioactive concentration of the reference object to be measured is valid. In the conventional nuclear medical diagnosis apparatus, in general, when the user determines that each of the normalization factor, the mutual calibration factor, and the radioactive concentration of the reference object to be measured is valid, the user may manually register each of the normalization factor, the mutual calibration factor, and the radioactive concentration of the reference object to be measured. Therefore, since the normalization factor, the mutual calibration factor, and the radioactive concentration of the reference object to be measured are automatically registered by registering the normalization factor, the mutual calibration factor, and the radioactive concentration of the reference object to be measured when the normalization unit, the calibration unit, and the quantitative value confirmation unit determine that the normalization factor, the mutual calibration factor, and the radioactive concentration of the reference object to be measured are valid, respectively, it is possible to further reduce the workload of the user.

Preferably, the nuclear medical diagnosis apparatus according to the first aspect further includes a hangar that stores the reference object to be measured for maintenance, and a carrying portion that carries the reference object to be measured for maintenance, wherein the carrying portion carries the reference object to be measured for maintenance to a measurement area before the reference data is acquired by the data acquisition unit and stores the reference object to be measured for maintenance in the hangar after the reference data is acquired. According to such a configuration, the reference object to be measured for maintenance may be automatically carried to the measurement area and automatically stored in the hangar. As a result, it is possible to reduce a workload of the user involved in measurement of the reference object to be measured for maintenance.

A nuclear medical diagnosis apparatus according to a second aspect of the invention includes a plurality of detectors that detects annihilation radiation emitted from a reference object to be measured, and a controller that acquires reference data of the reference object to be measured based on a result of detecting, by the plurality of detectors, the annihilation radiation emitted from the reference object to be measured, acquires a normalization factor for normalizing deviations of detection efficiencies among the plurality of detectors based on the reference data, acquires a mutual calibration factor for calibrating a pixel value of an image of the reference object to be measured acquired based on at least a part of the reference data used for acquisition of the normalization factor to radioactive concentration of the reference object to be measured, and compares radioactive concentration of the reference object to be measured calculated based on at least a part of the reference data used for acquisition of the normalization factor with a quantitative value of the radioactive concentration of the reference object to be measured.

In the nuclear medical diagnosis apparatus according to the second aspect of the invention, as described above, when the controller acquires the normalization factor based on the reference data, acquires the mutual calibration factor using at least a part of the reference data used for acquisition of the normalization factor, and calculates the radioactive concentration of the reference object to be measured, it is possible to acquire the normalization factor, acquire the mutual calibration factor, and calculate the radioactive concentration of the reference object to be measured using common data. In this way, when compared to a case in which data is separately acquired for each of acquisition of the normalization factor, acquisition of the mutual calibration factor, and calculation of the radioactive concentration of the reference object to be measured, it is possible to reduce the number of times of input of a parameter necessary for data acquisition, creation of the reference object to be measured, etc. in each process of routine maintenance and inspection of the apparatus, and thus it is possible to reduce a workload of a user. In addition, when compared to a case in which data is separately acquired, it is possible to shorten working hours since an effort to acquire data is omitted.

A method for routine maintenance and inspection of a nuclear medical diagnosis apparatus according to a third aspect of the invention includes acquiring reference data of a reference object to be measured based on a result of detecting, by a plurality of detectors, annihilation radiation emitted from the reference object to be measured, acquiring a normalization factor for normalizing deviations of detection efficiencies among the plurality of detectors based on the reference data, applying the normalization factor to at least a part of the reference data used for acquisition of the normalization factor to acquire a mutual calibration factor for calibrating a pixel value of a reconstructed image of the reference object to be measured to radioactive concentration of the reference object to be measured, and comparing radioactive concentration of the reference object to be measured calculated from a pixel value of an image of the reference object to be measured acquired by applying each of the normalization factor and the mutual calibration factor to at least a part of the reference data used for acquisition of the normalization factor with a quantitative value of the radioactive concentration of the reference object to be measured.

In the method for routine maintenance and inspection of the nuclear medical diagnosis apparatus according to the third aspect of the invention, as described above, when the normalization factor is acquired based on the reference data, the mutual calibration factor is acquired using at least apart of the reference data used for acquisition of the normalization factor, and the radioactive concentration of the reference object to be measured is calculated, it is possible to acquire the normalization factor, acquire the mutual calibration factor, and calculate the radioactive concentration of the reference object to be measured using common data. In this way, when compared to a case in which data is separately acquired for each of acquisition of the normalization factor, acquisition of the mutual calibration factor, and calculation of the radioactive concentration of the reference object to be measured, it is possible to reduce the number of times of input of a parameter necessary for data acquisition, creation of the reference object to be measured, etc. in each process of routine maintenance and inspection of the apparatus, and thus it is possible to reduce a workload of a user necessary for routine maintenance and inspection of the apparatus. In addition, it is possible to shorten time necessary for routine maintenance and inspection of the apparatus when compared to a case in which data is separately acquired.

DETAILED DESCRIPTION OF THE DRAWINGS

Hereinafter, embodiments embodying the invention will be described with reference to drawings.

(Outline of PET Device)

A description will be given of a configuration of a PET device 100 according to a first embodiment of the invention with reference to FIG. 1 to FIG. 4. The PET device 100 is an example of a "nuclear medical diagnosis apparatus" in claims.

The PET device 100 (see FIG. 1) is a device that captures an image of an inside of a human body using an agent labeled with a positron emitting radionuclide. Specifically, the PET device 100 is configured to acquire a location at which a pair of agents disappears by detecting a pair of annihilation radiation (gamma rays) generated by pair annihilation of an electron and a positron of the agent. Further, the PET device 100 may be configured to form (capture) an image of an inside of the human body by acquiring a plurality of locations at which pair annihilation of the agent occurs. Further, the formed image is used for diagnostic imaging of presence/absence of cancer cells.

Here, in routine maintenance and inspection of the PET device 100 (see FIG. 1), processes of normalization, cross-calibration, and quantitative value confirmation are performed. During these processes, a phantom 101 which is adjusted to predetermined radioactive concentration and emits a pair of annihilation radiation (gamma rays) is used as a reference object to be measured. The phantom 101 is an example of a "reference object to be measured" in claims.

(Configuration of PET Device)

Figure 1:
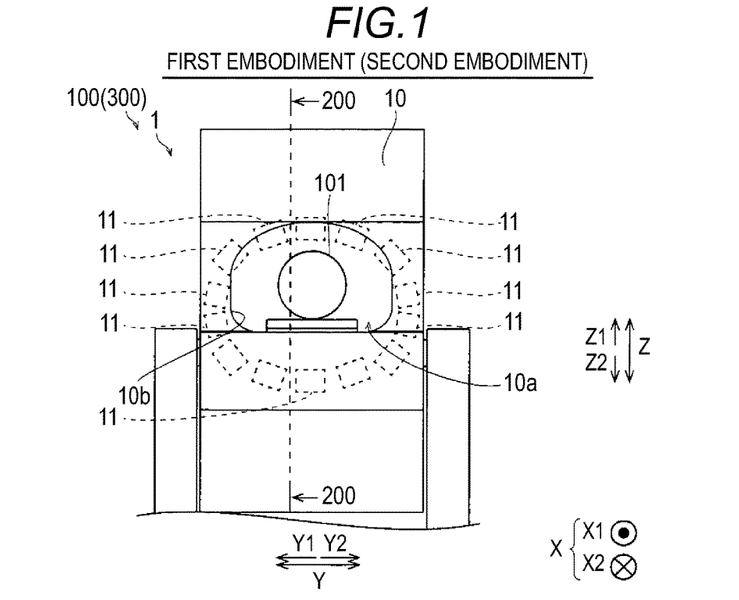
FIG. 1 is a schematic front view viewed in a direction in which a measurement area of a nuclear medical diagnosis apparatus according to first and second embodiments extends.

As illustrated in FIG. 1, a photographing unit 1 is provided in the PET device 100. In addition, the photographing unit 1 includes a housing 10.

In addition, the PET device 100 includes a plurality of (fourteen in the first embodiment) detectors 11. Specifically, the plurality of detectors 11 is disposed inside the housing 10. In addition, the plurality of detectors 11 is disposed to surround the phantom 101. Each of the detectors 11 detects annihilation radiation emitted from the phantom 101. In the first embodiment, the phantom 101 has a cylindrical shape. However, it is possible to adopt a ring shape or a linear shape. In addition, the phantom 101 is injected with FDG whose half-life is comparatively shorter than that of Ge-68 described below.

A measurement area 10a in which the phantom 101 is disposed is provided in the housing 10. The measurement area 10a includes a hole 10b penetrating the housing 10. In addition, the measurement area 10a is formed to extend in an X direction. The plurality of detectors 11 is disposed to surround the phantom 101 disposed inside the measurement area 10a on a surface perpendicular to the X direction in which the measurement area 10a extends. In this way, it is possible to reliably detect a pair of annihilation radiation rays emitted from a radiation source of the phantom 101 in mutually opposite directions using a pair of detectors 11 disposed to face each other across the radiation source.

Figure 2:
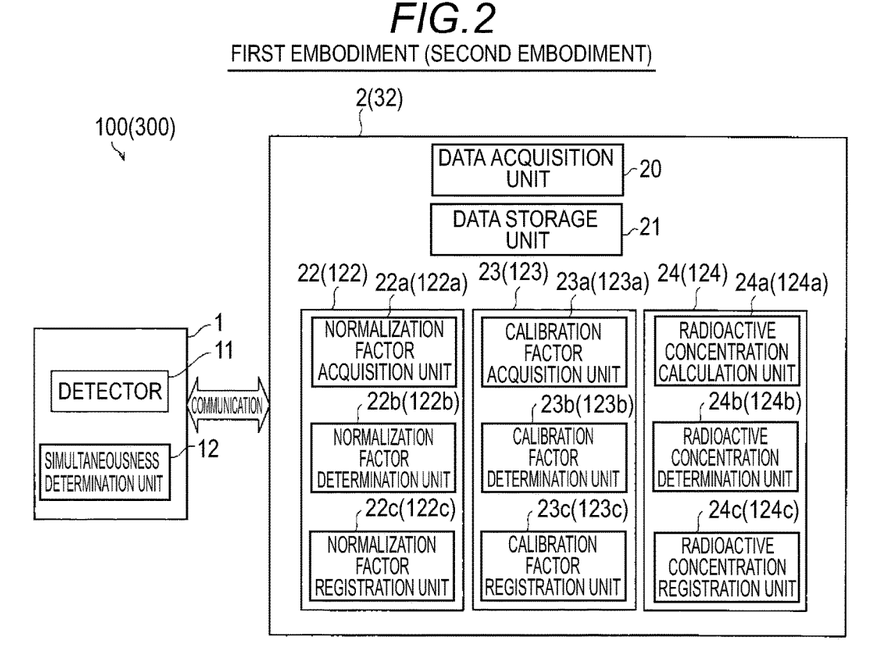
FIG. 2 is a block diagram illustrating a configuration of the nuclear medical diagnosis apparatus according to the first and second embodiments.

As illustrated in FIG. 2, the photographing unit 1 includes a simultaneousness determination unit 12. The simultaneousness determination unit 12 determines whether a pair of detectors 11 has detected annihilation radiation within a predetermined time difference (for example, several nanoseconds).

The PET device 100 includes a controller 2 configured to be able to communicate with the photographing unit 1. The controller 2 includes a data acquisition unit 20, a data storage unit 21, a normalization unit 22, a calibration unit 23, and a quantitative value confirmation unit 24. In addition, the normalization unit 22 includes a normalization factor acquisition unit 22a, a normalization factor determination unit 22b, and a normalization factor registration unit 22c. In addition, the calibration unit 23 includes a mutual calibration factor acquisition unit 23a, a mutual calibration factor determination unit 23b, and a mutual calibration factor registration unit 23c. In addition, the quantitative value confirmation unit 24 includes a radioactive concentration calculation unit 24a, a radioactive concentration determination unit 24b, and a radioactive concentration registration unit 24c. Each of the data acquisition unit 20, the normalization unit 22 (the normalization factor acquisition unit 22a, the normalization factor determination unit 22b, and the normalization factor registration unit 22c), the calibration unit 23 (the mutual calibration factor acquisition unit 23a, the mutual calibration factor determination unit 23b, and the mutual calibration factor registration unit 23c), and the quantitative value confirmation unit 24 (the radioactive concentration calculation unit 24a, the radioactive concentration determination unit 24b, and the radioactive concentration registration unit 24c) corresponds to a functional block as software in the controller 2. In addition, the data storage unit 21 is provided as hardware including a central processing unit (CPU), a memory, etc. in the controller 2.

The data acquisition unit 20 acquires reference data (see FIG. 3) (for example, data for two hours in the first embodiment) representing time dependency of radiation intensity of the radiation source of the phantom 101 based on a detection result of a pair of detectors 11 in a plurality of sets (a determination result of the simultaneousness determination unit 12). The reference data corresponds to data in the vicinity of radiation intensity at the time of medical practice.

Figure 3:
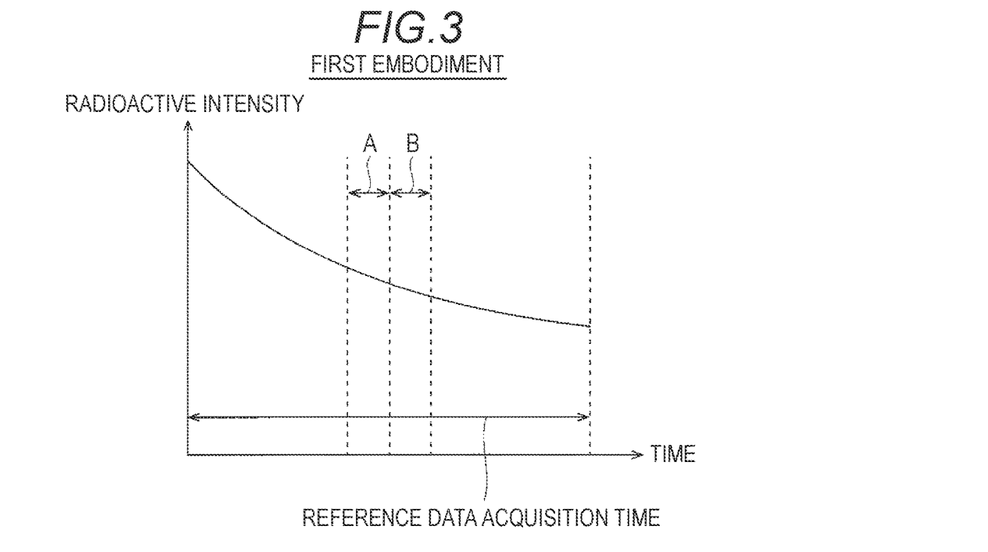
FIG. 3 is a diagram illustrating reference data of the nuclear medical diagnosis apparatus according to the first embodiment.

In normalization, the normalization factor acquisition unit 22a of the normalization unit 22 acquires a normalization factor for normalizing deviations of detection efficiencies among a plurality of sets of detectors 11 based on the reference data (see FIG. 3). In this case, the normalization factor acquisition unit 22a acquires the normalization factor using all the acquired reference data. In addition, the acquired reference data is stored in the data storage unit 21.

Here, in the first embodiment, in cross-calibration, the calibration unit 23 acquires an image of the phantom 101 reconstructed by applying the normalization factor to a part of the reference data (see FIG. 3) (for example, data for five minutes in the first embodiment) used for acquisition of the normalization factor. Further, the mutual calibration factor acquisition unit 23a of the calibration unit 23 acquires a mutual calibration factor for calibrating a pixel value (cps/ml) of the image of the phantom 101 acquired by the calibration unit 23 to radioactive concentration (Bq/ml) of the phantom 101. Specifically, the mutual calibration factor acquisition unit 23a acquires a mutual calibration factor for calibrating an average value of an area in which the pixel value of the image of the phantom 101 acquired by the calibration unit 23 is uniform to radioactive concentration (Bq/ml) of the phantom 101. Then, as described below, validity of the acquired mutual calibration factor is determined by the mutual calibration factor determination unit 23b of the calibration unit 23.

In addition, in quantitative value confirmation, the quantitative value confirmation unit 24 acquires an image of the phantom 101 by applying each of the normalization factor and the mutual calibration factor to a part of the reference data (see FIG. 3) (for example, data for five minutes in the first embodiment) used for acquisition of the normalization factor. Further, the radioactive concentration calculation unit 24a of the quantitative value confirmation unit 24 calculates radioactive concentration (Bq/ml) of the phantom 101 from a pixel value (Bq/ml) of an image of the phantom 101 acquired by the quantitative value confirmation unit 24. Specifically, the radioactive concentration calculation unit 24a calculates an average value of an area in which the pixel value of the image of the phantom 101 acquired by the quantitative value confirmation unit 24 is uniform. Then, the quantitative value confirmation unit 24 compares radioactive concentration (the average value of the area in which the pixel value is uniform) of the phantom 101 calculated by the radioactive concentration calculation unit 24a with a quantitative value of radioactive concentration of the phantom 101 acquired in advance (adjusted to predetermined concentration in advance).

In addition, in the first embodiment, the data acquisition unit 20 is configured to acquire reference data by performing measurement once. That is, the data acquisition unit 20 acquires one piece of continuous data as reference data.

In addition, in the first embodiment, as illustrated in FIG. 3, the calibration unit 23 designates calibration data used for image reconstruction corresponding to the area A which is a part of the reference data. Then, the mutual calibration factor acquisition unit 23a of the calibration unit 23 acquires mutual calibration factor by applying the normalization factor to the designated calibration data to reconstruct the image. In addition, the quantitative value confirmation unit 24 designates confirmation data corresponding to an area B which is a part of the reference data. Further, the radioactive concentration calculation unit 24a of the quantitative value confirmation unit 24 is configured to calculate radioactive concentration of the phantom 101 by applying each of the normalization factor and the mutual calibration factor to the designated confirmation data. The area A and the area B correspond to continuous areas. The area A and the area B have substantially equal lengths. In addition, a time of transition from the area A to the area B corresponds to substantially a midpoint of a reference data acquisition time. The area A and the area B are examples of a "first area" and a "second area" in claims, respectively.

In addition, in the first embodiment, when a difference between a normalization factor acquired this time and a normalization factor acquired at a previous time is within a first ratio (for example, 20%) of the normalization factor acquired at the previous time, the normalization unit 22 (the normalization factor determination unit 22b) determines that the normalization factor acquired this time is valid. In addition, when a difference between a mutual calibration factor acquired this time and a mutual calibration factor acquired at a previous time is within a second ratio (for example, 5%) of the mutual calibration factor acquired at the previous time, the calibration unit 23 (the mutual calibration factor determination unit 23b) determines that the mutual calibration factor acquired this time is valid. In addition, when a difference between calculated radioactive concentration of the phantom 101 and a quantitative value of radioactive concentration of the phantom 101 acquired in advance is within a third ratio (for example, 5%) of the quantitative value of the radioactive concentration of the phantom 101 acquired in advance, the quantitative value confirmation unit 24 (the radioactive concentration determination unit 24b) determines that the radioactive concentration of the phantom 101 calculated this time is valid. The first ratio is a threshold value used for determination for each pair of detectors 11 in the plurality of sets, and thus is set to be relatively larger than the second ratio and the third ratio. In this way, it is possible to relax a criterion for determination of the normalization factor, and to shorten time required for determining the normalization factor. In addition, it is preferable that the second ratio and the third ratio are set to substantially equal values.

In addition, in the first embodiment, when it is determined that the normalization factor is valid, the normalization unit 22 registers the normalization factor. In addition, when it is determined that the mutual calibration factor is valid, the calibration unit 23 registers the mutual calibration factor. When it is determined that the radioactive concentration of the phantom 101 calculated by the radioactive concentration calculation unit 24a is valid, the quantitative value confirmation unit 24 is configured to register the calculated radioactive concentration of the phantom 101. Specifically, when the normalization factor determination unit 22b determines that the normalization factor is valid, the normalization factor registration unit 22c registers the normalization factor. When the mutual calibration factor determination unit 23b determines that the mutual calibration factor is valid, the mutual calibration factor registration unit 23c registers the mutual calibration factor. When the radioactive concentration determination unit 24b determines that the radioactive concentration of the phantom 101 calculated by the radioactive concentration calculation unit 24a is valid, the radioactive concentration registration unit 24c registers the calculated radioactive concentration of the phantom 101. Each of the normalization factor, the mutual calibration factor, and the radioactive concentration of the phantom 101 determined to be valid is stored (registered) in the data storage unit 21.

(Control Flow of Controller)

Figure 4:
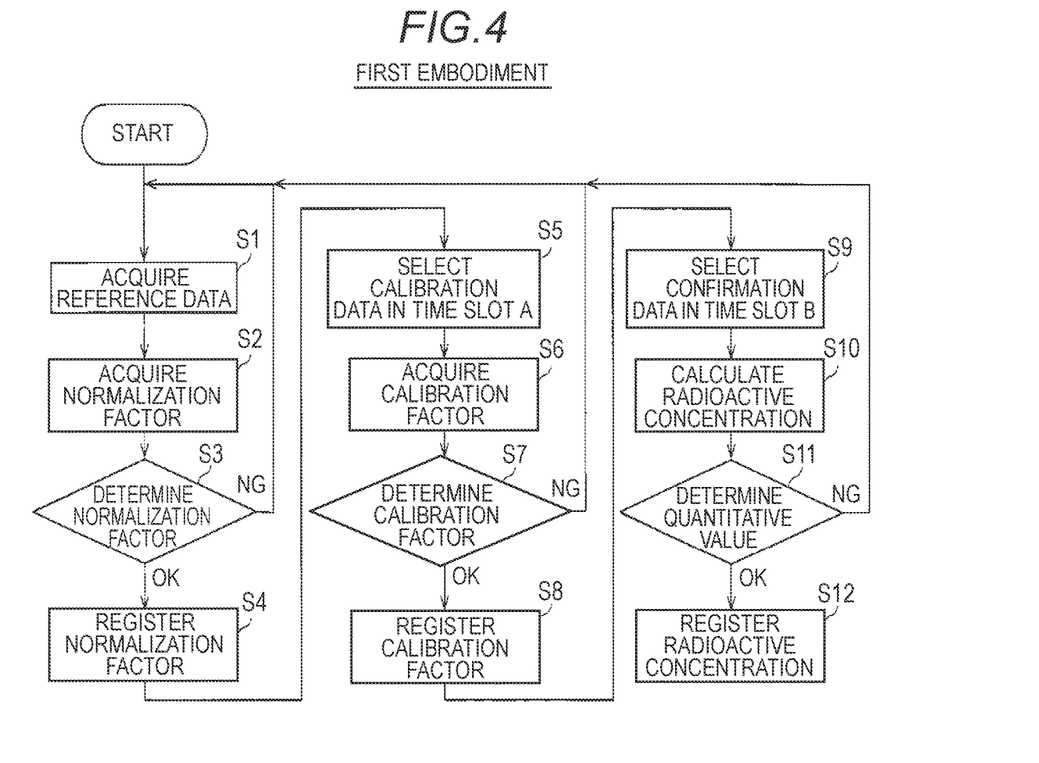
FIG. 4 is a flowchart for description of a control flow of a controller of the nuclear medical diagnosis apparatus according to the first embodiment.

Next, a description will be given of a control flow of the controller 2 of the PET device 100 (see FIG. 1) of the first embodiment with reference to FIG. 4.

First, in step S1, reference data is acquired by the data acquisition unit 20.

Subsequently, in step S2, a normalization factor is acquired by the normalization factor acquisition unit 22*a* based on the reference data acquired in step S1.

Subsequently, in step S3, the normalization factor determination unit 22*b* determines whether the normalization factor acquired in step S2 is valid. When it is determined that the acquired normalization factor is valid, the operation proceeds to step S4. In addition, when it is determined that the acquired normalization factor is not valid, the operation returns to step S1. When it is repeatedly determined that the normalization factor is not valid, an error may be displayed on the assumption that the PET device 100 has abnormality.

Subsequently, in step S4, the normalization factor acquired in step S2 is registered by the normalization factor registration unit 22*c*.

Subsequently, in step S5, calibration data in the area A in the reference data is designated by the calibration unit 23.

Subsequently, in step S6, a mutual calibration factor is acquired by the mutual calibration factor acquisition unit 23*a* based on the calibration data designated in step S5.

Subsequently, in step S7, validity of the mutual calibration factor acquired in step S6 is determined by the mutual calibration factor determination unit 23*b*. When it is determined that the acquired mutual calibration factor is valid, the operation proceeds to step S8. When it is determined that the acquired mutual calibration factor is not valid, the operation returns to step S1. When it is repeatedly determined that the mutual calibration factor is not valid, an error may be displayed on the assumption that the PET device 100 has abnormality.

Subsequently, in step S8, the normalization factor acquired in step S6 is registered by the mutual calibration factor registration unit 23*c*.

Subsequently, in step S9, confirmation data in the area B in the reference data is designated by the quantitative value confirmation unit 24.

Subsequently, in step S10, radioactive concentration of the phantom 101 is calculated by the radioactive concentration calculation unit 24*a* based on the confirmation data designated in step S9.

Subsequently, in step S11, validity of the radioactive concentration of the phantom 101 calculated in step S10 is determined by the radioactive concentration determination unit 24*b*. When it is determined that the calculated radioactive concentration of the phantom 101 is valid, the operation proceeds to step S12. When it is determined that the calculated radioactive concentration of the phantom 101 is not valid, the operation returns to step S1. When it is repeatedly determined that the radioactive concentration of the phantom 101 is not valid, an error may be displayed on the assumption that the PET device 100 has abnormality.

Subsequently, in step S12, the radioactive concentration of the phantom 101 calculated in step S10 is registered by the radioactive concentration registration unit 24*c*.

In the first embodiment, it is possible to obtain the following effects.

In the first embodiment, as described above, the PET device 100 is configured to include the data acquisition unit 20 that acquires reference data of the phantom 101, the normalization unit 22 that acquires a normalization factor for normalizing deviations of detection efficiencies among the plurality of detectors 11 based on the reference data, the calibration unit 23 that applies the normalization factor to a part of the reference data used for acquisition of the normalization factor and acquires a mutual calibration factor for calibrating a pixel value of a reconstructed image of the phantom 101 to radioactive concentration of the phantom 101, and the quantitative value confirmation unit 24 that compares the radioactive concentration of the phantom 101 calculated from the pixel value of the image of the phantom 101 acquired by applying each of the normalization factor and the mutual calibration factor to the part of the reference data used for acquisition of the normalization factor with a quantitative value of the radioactive concentration of the phantom 101. In this way, acquisition of the normalization factor, acquisition of the mutual calibration factor, and calculation of the radioactive concentration of the phantom 101 may be performed using common data. As a result, when compared to a case in which data is separately acquired for each of acquisition of the normalization factor, acquisition of the mutual calibration factor, and calculation of the radioactive concentration of the phantom 101, it is possible to reduce the number of times of input of a parameter necessary for data acquisition, creation of the phantom 101, etc. in each process of routine maintenance and inspection of the apparatus, and thus it is possible to reduce a workload of a user. In addition, it is possible to shorten working hours when compared to a case in which data is separately acquired.

In addition, in a conventional PET device, the phantom 101 may be created only for acquisition of the mutual calibration factor and quantitative value confirmation of the radioactive concentration of the phantom 101. When compared to this case, it is possible to omit an effort to create the phantom 101, and thus it is possible to effectively reduce the workload of the user. In addition, since the phantom 101 is created only once, it is possible to prevent occurrence of a measurement error due to a deviation of radioactive concentration of the created phantom 101.

In addition, in the first embodiment, as described above, the PET device 100 is configured so that the data acquisition unit 20 acquires reference data by performing measurement once. In this way, when compared to a case in which data is acquired a plurality of times, it is possible to further reduce the workload of the user. In addition, since measurement is performed only once, the number of parameter inputs required each time measurement is performed can be reduced to once. As a result, occurrence of an erroneous input of a parameter can be suppressed.

In addition, in the first embodiment, as described above, the calibration unit 23 designates calibration data used for image reconstruction corresponding to the area A which is a part of the reference data, and acquires the mutual calibration factor by applying the normalization factor to the calibration data to reconstruct the image. Further, the PET device 100 is configured such that the quantitative value confirmation unit 24 designates confirmation data corresponding to the area B which is a part of the reference data and calculates radioactive concentration of the phantom 101 by applying each of the normalization factor and the mutual calibration factor to the confirmation data. In this way, it is possible to arbitrarily designate the calibration data and the confirmation data from the reference data. As a result, it is possible to easily acquire data suitable for a condition of radiation intensity, etc. required by the user.

In addition, in the first embodiment, as described above, when the difference between the normalization factor acquired this time and the normalization factor acquired at the previous time is within the first ratio, the normalization unit 22 (the normalization factor determination unit 22*b*) determines that the normalization factor acquired this time is valid. In addition, when it is determined that the difference between the mutual calibration factor acquired this time and the mutual calibration factor acquired at the previous time is within the second ratio, the calibration unit 23 (the mutual calibration factor determination unit 23b) determines that the mutual calibration factor acquired this time is valid. In addition, when the difference between the calculated radioactive concentration of the phantom 101 and the quantitative value of the radioactive concentration of the phantom 101 acquired in advance is within the third ratio of the quantitative value of the radioactive concentration of the phantom 101 acquired in advance, the quantitative value confirmation unit 24 (the radioactive concentration determination unit 24b) determines that the radioactive concentration of the phantom 101 calculated this time is valid. In this way, the PET device 100 is configured. Here, in a conventional nuclear medical diagnosis apparatus, in general, the user determines validity of each of the normalization factor, the mutual calibration factor, and the radioactive concentration of the reference object to be measured (the phantom, etc.). Therefore, when the normalization unit 22 (the normalization factor determination unit 22b), the calibration unit 23 (the mutual calibration factor determination unit 23b), and the quantitative value confirmation unit 24 (the radioactive concentration determination unit 24b) determine validities of the normalization factor, the mutual calibration factor, and the radioactive concentration of the phantom 101, respectively, it is possible to further reduce the workload of the user. In addition, when compared to a case in which the user determines validities of the normalization factor, the mutual calibration factor, and the radioactive concentration of the phantom 101, it is possible to suppress occurrence of an artificial deviation in a determination result.

In addition, in the first embodiment, as described above, when it is determined that the normalization factor is valid, the normalization unit 22 registers the normalization factor. In addition, when it is determined that the mutual calibration factor is valid, the calibration unit 23 registers the mutual calibration factor. In addition, the PET device 100 is configured such that when it is determined that the calculated radioactive concentration of the phantom 101 is valid, the quantitative value confirmation unit 24 registers the calculated radioactive concentration of the phantom 101. In the conventional nuclear medical diagnosis apparatus, in general, when the user determines that each of the normalization factor, the mutual calibration factor, and the radioactive concentration of the reference object to be measured (the phantom, etc.) is valid, the user manually register each of the normalization factor, the mutual calibration factor, and the radioactive concentration of the reference object to be measured (the phantom, etc.). Therefore, since the normalization factor, the mutual calibration factor, and the radioactive concentration of the phantom 101 are automatically registered by registering the normalization factor, the mutual calibration factor, and the radioactive concentration of the phantom 101 when the normalization unit 22, the calibration unit 23, and the quantitative value confirmation unit 24 determine that the normalization factor, the mutual calibration factor, and the radioactive concentration of the phantom 101 are valid, respectively, it is possible to further reduce the workload of the user.

In addition, in the first embodiment, as described above, the PET device 100 is configured to include a controller 2 that acquires reference data, acquires a normalization factor for normalizing deviations of detection efficiencies among a plurality of detectors 11 based on the reference data, acquires a mutual calibration factor for calibrating a pixel value of an image of the phantom 101 acquired based on a part of the reference data used for acquisition of the normalization factor to radioactive concentration of the phantom 101, and compares the radioactive concentration of the phantom 101 calculated based on the part of the reference data used for acquisition of the normalization factor with a quantitative value of the radioactive concentration of the phantom 101. In this way, it is possible to perform acquisition of the normalization factor, acquisition of the mutual calibration factor, and calculation of the radioactive concentration of the phantom 101 using common data. As a result, when compared to a case in which data is separately acquired for each of acquisition of the normalization factor, acquisition of the mutual calibration factor, and calculation of the radioactive concentration of the phantom 101, it is possible to reduce the number of times of input of a parameter necessary for data acquisition, creation of the phantom. 101, etc. in each process of routine maintenance and inspection of the apparatus, and thus it is possible to reduce the workload of the user. In addition, it is possible to shorten working hours when compared to a case in which data is separately acquired.

In addition, in the first embodiment, as described above, a method for routine maintenance and inspection of the PET device 100 is configured to include a process of acquiring reference data of the phantom 101 based on a result of detecting annihilation radiation emitted from the phantom 101 by the plurality of detectors 11, a process of acquiring a normalization factor for a normalizing deviations of detection efficiencies among the plurality of detectors based on the reference data, a process of applying the normalization factor to at least a part of the reference data used for acquisition of the normalization factor to acquire a mutual calibration factor for calibrating a pixel value of a reconstructed image of the phantom 101 to radioactive concentration of the phantom 101, and a process of comparing radioactive concentration of the phantom 101 calculated from a pixel value of an image of the phantom 101 acquired by applying each of the normalization factor and the mutual calibration factor to at least the part of the reference data used for acquisition of the normalization factor with a quantitative value of the radioactive concentration of the phantom 101. In this way, it is possible to perform acquisition of the normalization factor, acquisition of the mutual calibration factor, and calculation of the radioactive concentration of the phantom 101 using common data. In this way, when compared to a case in which data is separately acquired for each of acquisition of the normalization factor, acquisition of the mutual calibration factor, and calculation of the radioactive concentration of the phantom 101, it is possible to reduce the number of times of input of a parameter necessary for data acquisition, creation of the phantom 101, etc. in each process of routine maintenance and inspection of the apparatus, and thus it is possible to reduce the workload of the user necessary for routine maintenance and inspection of the apparatus. In addition, it is possible to shorten time necessary for routine maintenance and inspection of the apparatus when compared to a case in which data is separately acquired.

Next, a description will be given of a configuration of a PET device 300 according to a second embodiment of the invention with reference to FIG. 2, FIG. 5, and FIG. 6. In the second embodiment, a description will be given of an example in which a plurality of pieces of calibration data and a plurality of pieces of confirmation data are designated from reference data unlike the first embodiment in which one piece of calibration data and one piece of confirmation data are designated from reference data. The same reference numeral will be assigned to the same configuration as that of the first embodiment, and a description thereof will be omitted. In addition, the PET device 300 is an example of a "nuclear medical diagnosis apparatus" in claims.

(Configuration of PET Device)

As illustrated in FIG. 2, the PET device 300 includes a controller 32. The controller 32 includes a normalization unit 122, a calibration unit 123, and a quantitative value confirmation unit 124. In addition, the normalization unit 122 includes a normalization factor acquisition unit 122a, a normalization factor determination unit 122b, and a normalization factor registration unit 122c. In addition, the calibration unit 123 includes a mutual calibration factor acquisition unit 123a, a mutual calibration factor determination unit 123b, and a mutual calibration factor registration unit 123c. In addition, the quantitative value confirmation unit 124 includes a radioactive concentration calculation unit 124a, a radioactive concentration determination unit 124b, and a radioactive concentration registration unit 124c. Each of the normalization unit 122 (the normalization factor acquisition unit 122a, the normalization factor determination unit 122b, and the normalization factor registration unit 122c), the calibration unit 123 (the mutual calibration factor acquisition unit 123a, the mutual calibration factor determination unit 123b, and the mutual calibration factor registration unit 123c), and the quantitative value confirmation unit 124 (the radioactive concentration calculation unit 124a, the radioactive concentration determination unit 124b, and the radioactive concentration registration unit 124c) corresponds to a functional block as software in the controller 32.

Figure 5:
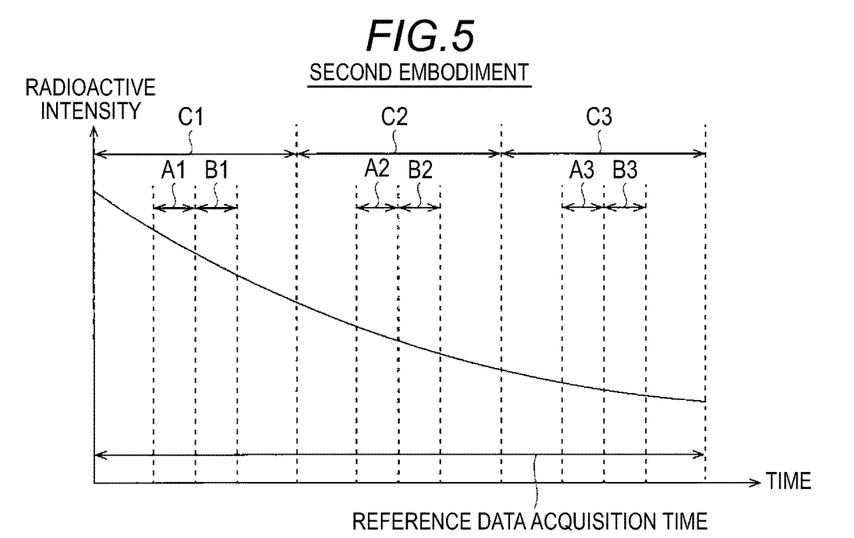
FIG. 5 is a diagram illustrating reference data of the nuclear medical diagnosis apparatus according to the second embodiment.
Figure 6:
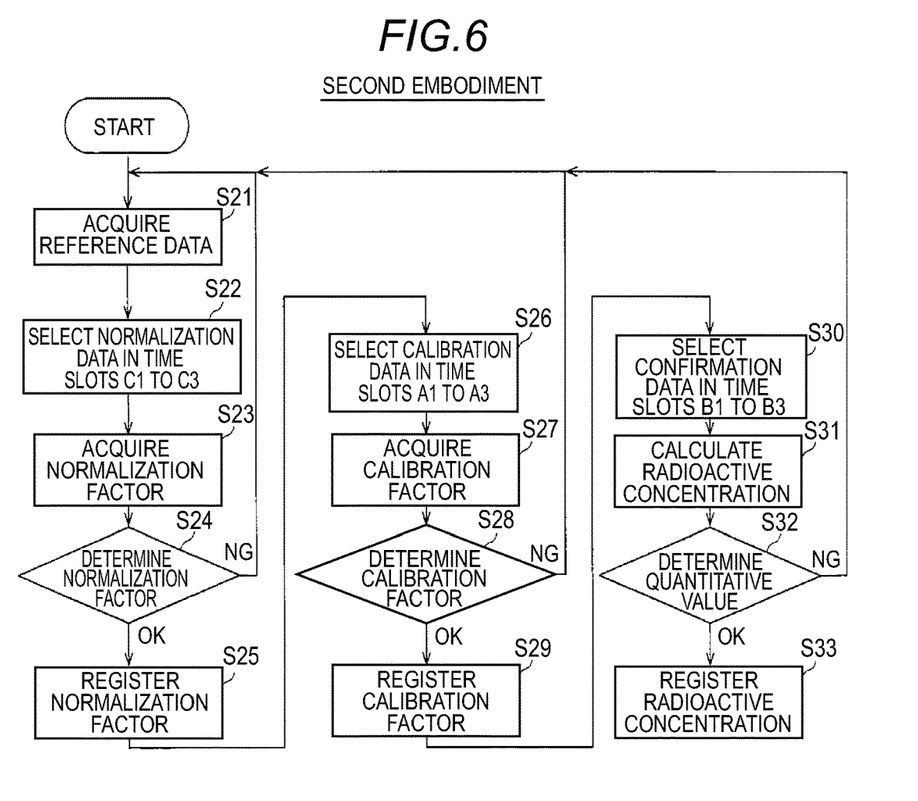
FIG. 6 is a flowchart for description of a control flow of a controller of the nuclear medical diagnosis apparatus according to the second embodiment.

In the second embodiment, as illustrated in FIG. 5, the calibration unit 123 is configured to designate a plurality of (three in the second embodiment) different pieces of calibration data corresponding to a plurality of (three in the second embodiment) different areas A1 to A3 (for example, each of which corresponds to data for five minutes in the second embodiment), respectively, in reference data (for example, data for six hours in the second embodiment) continuously acquired in areas C1 to C3 (for example, each of which corresponds to data for two hours in the second embodiment). In addition, the calibration unit 123 is configured to acquire a plurality of (three in the second embodiment) mutual calibration factors corresponding to the plurality of respective pieces of calibration data. Each of the areas A1 to A3 is an example of a "first area" in claims.

Specifically, the normalization unit 122 acquires normalization data in the area C1 in the reference data. Further, the normalization factor acquisition unit 122a acquires a normalization factor in the area C1. In addition, the calibration unit 123 acquires calibration data in the area A1 which is a part of the area C1. Further, the mutual calibration factor acquisition unit 123a acquires a mutual calibration factor in the area A1 by applying the normalization factor in the area C1 to the calibration data in the area A1. Similarly, the mutual calibration factor acquisition unit 123a acquires a mutual calibration factor in the area A2 which is a part of the area C2, and acquires a mutual calibration factor in the area A3 which is a part of the area C3. The areas C1 to C3 do not overlap with each other. At least a part of the reference data corresponds to data in the vicinity of radiation intensity at the time of medical practice.

In the PET device 300, counting loss correction factors corresponding to the respective areas A1 to A3 are acquired based on the respective mutual calibration factors acquired corresponding to the plurality of different areas A1 to A3, respectively. Counting loss means that apart of annihilation radiation emitted from the radiation source of the phantom 101 is not detected by a detector 11.

In the second embodiment, the quantitative value confirmation unit 124 is configured to designate a plurality of (three in the second embodiment) different pieces of confirmation data corresponding to a plurality of (three in the second embodiment) different areas B1 to B3 (for example, each of which corresponds to data for five minutes in the second embodiment), respectively, in the reference data. In addition, the quantitative value confirmation unit 124 is configured to calculate radioactive concentration of the phantom 101 corresponding to each of the plurality of pieces of confirmation data. Each of the areas B1 to B3 is an example of a "second area" in claims.

Specifically, the quantitative value confirmation unit 124 acquires confirmation data in the area B1 which is a part of the area C1. Further, the radioactive concentration calculation unit 124a applies the normalization factor in the area C1 and the mutual calibration factor in the area A1 to the confirmation data in the area B1. In this way, the radioactive concentration calculation unit 124a calculates radioactive concentration of the phantom 101 using the confirmation data in the area B1. Similarly, the radioactive concentration calculation unit 124a calculates radioactive concentration of the phantom 101 by applying the normalization factor in the area C2 and the mutual calibration factor in the area A2 to the confirmation data in the area B2. In addition, the radioactive concentration calculation unit 124a calculates radioactive concentration of the phantom 101 by applying the normalization factor in the area C3 and the mutual calibration factor in the area A3 to the confirmation data in the area B3. Each of the area A1 and the area B1, the area A2 and the area B2, and the area A3 and the area B3 corresponds to a continuous area. In addition, a time of transition from the area A1 to the area B1, a time of transition from the area A2 to the area B2, and a time of transition from the area A3 to the area B3 correspond to substantially midpoints of the area C1, the area C2, and the area C3, respectively.

In addition, in the second embodiment, when a difference between a normalization factor acquired this time and a normalization factor acquired at a previous time is within a first ratio (for example, 20%) of the normalization factor acquired at the previous time in each of the areas C1 to C3, the normalization unit 122 (the normalization factor determination unit 122b) determines that the normalization factor acquired this time is valid. In addition, when a difference between a mutual calibration factor acquired this time and a mutual calibration factor acquired at a previous time is within a second ratio (for example, 5%) of the mutual calibration factor acquired at the previous time in each of the areas A1 to A3, the calibration unit 123 (the mutual calibration factor determination unit 123b) determines that the mutual calibration factor acquired this time is valid. In addition, when a difference between calculated radioactive concentration of the phantom 101 and a quantitative value of radioactive concentration of the phantom 101 acquired in advance is within a third ratio (for example, 5%) of the quantitative value of the radioactive concentration of the phantom 101 acquired in advance in each of the areas B1 to B3, the quantitative value confirmation unit 124 (the radioactive concentration determination unit 124b) determines that the radioactive concentration of the phantom 101 calculated this time is valid.

In addition, in the second embodiment, when it is determined that the normalization factor is valid, the normalization unit 122 registers the normalization factor by associating the normalization factor with the area (the area C1, the area C2, or the area C3) in which the normalization factor is acquired. In addition, when it is determined that the mutual calibration factor is valid, the calibration unit 123 registers the mutual calibration factor by associating the mutual calibration factor with the area (the area A1, the area A2, or the area A3) in which the mutual calibration factor is acquired. In addition, when it is determined that the radioactive concentration of the phantom 101 calculated by the radioactive concentration calculation unit 124a is valid, the quantitative value confirmation unit 124 is configured to register the calculated radioactive concentration of the phantom 101 by associating the calculated radioactive concentration with the area (the area B1, the area B2, or the area B3) in which the radioactive concentration of the phantom 101 is calculated.

Specifically, when the normalization factor determination unit 122b determines that the normalization factor is valid, the normalization factor registration unit 122c registers the normalization factor by associating the normalization factor with the area (the area C1, the area C2, or the area C3) in which the normalization factor is acquired. In addition, when the mutual calibration factor determination unit 123b determines that the mutual calibration factor is valid, the mutual calibration factor registration unit 123c registers the mutual calibration factor by associating the mutual calibration factor with the area (the area A1, the area A2, or the area A3) in which the mutual calibration factor is acquired. In addition, when the radioactive concentration determination unit 124b determines that the radioactive concentration of the phantom 101 calculated by the radioactive concentration calculation unit 124a is valid, the radioactive concentration registration unit 124c registers the calculated radioactive concentration of the phantom 101 by associating the calculated radioactive concentration with the area (the area B1, the area B2, or the area B3) in which the radioactive concentration of the phantom 101 is calculated.

(Control Flow of Controller)

Next, a description will be given of a control flow of the controller 32 of the PET device 300 (see FIG. 1) according to the second embodiment with reference to FIG. 6.

First, in step S21, reference data is acquired by the data acquisition unit 20.

Subsequently, in step S22, normalization data in each of the areas C1 to C3 is designated.

Subsequently, in step S23, a normalization factor in each of the areas C1 to C3 is acquired by the normalization factor acquisition unit 122a based on the normalization data acquired in step S22.

Subsequently, in step S24, the normalization factor determination unit 122b determines whether each normalization factor acquired in step S23 is valid. When it is determined that all the acquired normalization factors are valid, the operation proceeds to step S25. In addition, when it is determined that even one of the acquired normalization factors is not valid, the operation returns to step S21. When it is repeatedly determined that the normalization factor is not valid, an error may be displayed on the assumption that the PET device 300 has abnormality.

Subsequently, in step S25, each normalization factor acquired in step S23 is registered by the normalization factor registration unit 122c.

Subsequently, in step S26, calibration data in each of the areas A1 to A3 in the reference data is designated by the calibration unit 123.

Subsequently, in step S27, a mutual calibration factor in each of the areas A1 to A3 is acquired by the mutual calibration factor acquisition unit 123a based on the calibration data designated in step S26.

Subsequently, in step S28, the mutual calibration factor determination unit 123b determines validity of each mutual calibration factor acquired in step S27. When it is determined that all the acquired mutual calibration factors are valid, the operation proceeds to step S29. In addition, when it is determined that even one of the acquired mutual calibration factors is not valid, the operation returns to step S21. When it is repeatedly determined that the mutual calibration factor is not valid, an error may be displayed on the assumption that the PET device 300 has abnormality.

Subsequently, in step S29, each mutual calibration factor acquired in step S27 is registered by the mutual calibration factor registration unit 123c.

Subsequently, in step S30, confirmation data in each of the areas B1 to B3 in the reference data is designated by the quantitative value confirmation unit 124.

Subsequently, in step S31, the radioactive concentration calculation unit 124a calculates radioactive concentration of the phantom 101 in each of the areas B1 to B3 based on the confirmation data designated in step S30.

Subsequently, in step S32, the radioactive concentration determination unit 124b determines validity of each radioactive concentration of the phantom 101 calculated in step S31. When it is determined that all the calculated radioactive concentrations of the phantom 101 are valid, the operation proceeds to step S33. In addition, when it is determined that even one of the calculated radioactive concentrations of the phantom 101 is not valid, the operation returns to step S21. When it is repeatedly determined that the radioactive concentration of the phantom 101 is not valid, an error may be displayed on the assumption that the PET device 300 has abnormality.

Subsequently, in step S33, each radioactive concentration of the phantom 101 calculated in step S31 is registered by the radioactive concentration registration unit 124c.

The other configurations of the second embodiment are the same as those of the first embodiment.

In the second embodiment, it is possible to obtain the following effects.

In the second embodiment, as described above, the PET device 300 is configured such that the calibration unit 123 designates calibration data corresponding to each of the plurality of different areas A1 to A3 in the reference data to acquire a plurality of mutual calibration factors corresponding to the plurality of respective pieces of calibration data. In this way, it is possible to easily acquire and evaluate the mutual calibration factor corresponding to the radiation intensity of the radiation source by designating the plurality of pieces of calibration data from one piece of reference data. As a result, it is possible to effectively reduce the workload of the user when compared to a case in which the calibration data is separately acquired a plurality of times to acquire and evaluate the mutual calibration factor corresponding to the radiation intensity of the radiation source.

When the radioactive concentration of the radiation source is high, the number of annihilation radiation rays emitted from the radiation source is relatively large, and thus a possibility of occurrence of counting loss of annihilation radiation by the detector 11 increases. Therefore, when a counting loss correction factor is acquired based on a mutual calibration factor acquired after radioactive concentration of the radiation source decreases as in the conventional nuclear medical diagnosis apparatus, counting loss may not be accurately corrected in an area in which the radioactive concentration of the radiation source is high. For this reason, the conventional nuclear medical diagnosis apparatus separately requires a process for correcting counting loss apart from a cross-calibration process of acquiring a mutual calibration factor.

On the contrary, in the second embodiment, since the mutual calibration factor corresponding to the radiation intensity of the radiation source may be acquired by acquiring the mutual calibration factor corresponding to each of the plurality of different areas A1 to A3, it is possible to acquire the counting loss correction factor corresponding to the radiation intensity of the radiation source based on each acquired mutual calibration factor. That is, when the calibration factor corresponding to the radiation intensity of the radiation source is acquired, the counting loss correction factor corresponding to the radiation intensity of the radiation source may be acquired at the same time, and thus a process for correcting the counting loss may not be separately performed. In this way, it is possible to suppress an increase in maintenance workload.

In addition, in the second embodiment, as described above, the PET device 300 is configured such that the quantitative value confirmation unit 124 calculates the radioactive concentration of the phantom 101 corresponding to each of the plurality of pieces of confirmation data by designating the confirmation data corresponding to each of the plurality of different areas B1 to B3 in the reference data. In this way, it is possible to easily perform quantitative value confirmation for the radioactive concentration of the phantom 101 corresponding to the radiation intensity of the radiation source by designating the plurality of pieces of confirmation data from the one piece of reference data. As a result, it is possible to effectively reduce the workload of the user when compared to a case in which confirmation data is separately acquired a plurality of times to perform quantitative value confirmation for the radioactive concentration of the phantom 101 corresponding to the radiation intensity of the radiation source.

The other effects of the second embodiment are the same as those of the first embodiment.

It should be considered that the embodiment disclosed this time is an example in all respects and is not restrictive. The scope of the invention is indicated not by the description of the above embodiment and by the scope of claims, and includes meanings equivalent to the scope of claims and all changes (modifications) within the scope.

Figure 7:
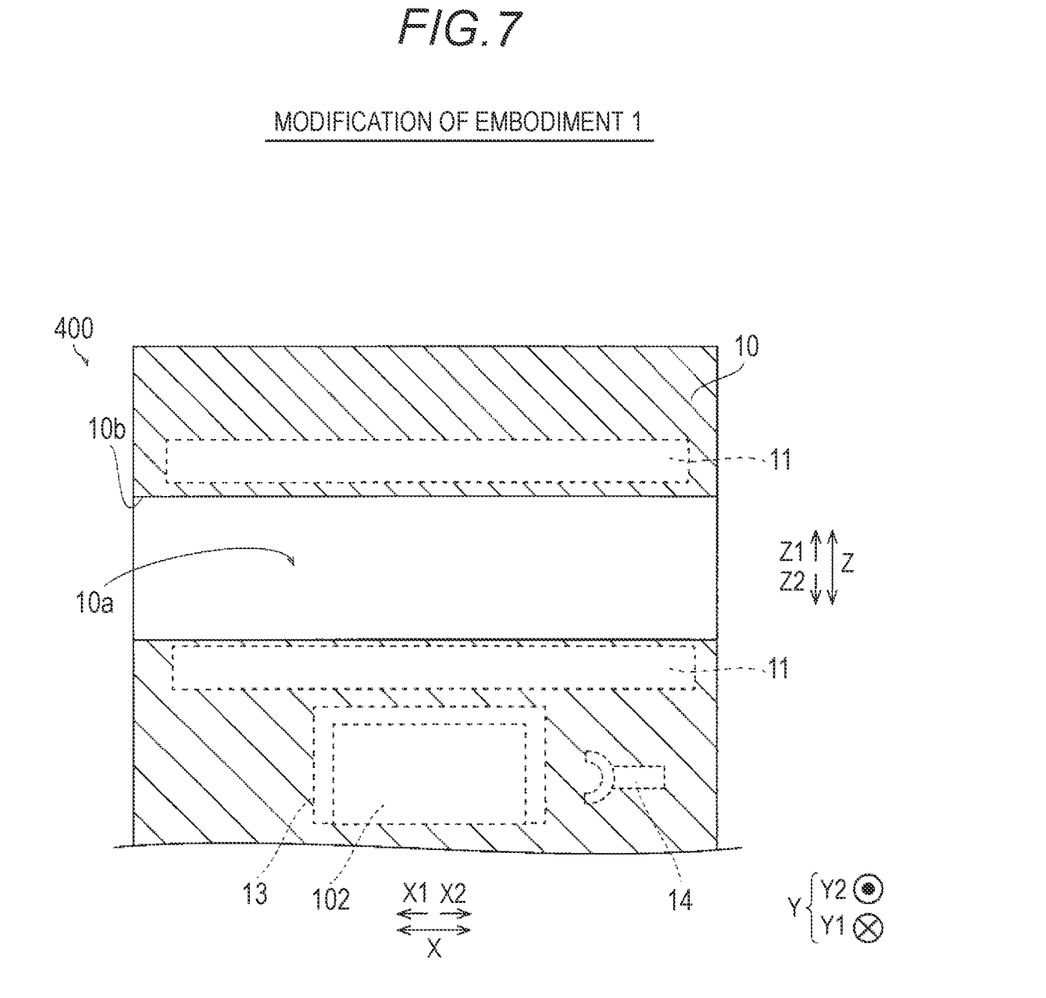
FIG. 7 is a cross-sectional view of a nuclear medical diagnosis apparatus according to a modification of the first embodiment taken along 200-200 line of FIG. 1.

For example, as illustrated in FIG. 7, a PET device 400 includes a hangar 13 that stores a maintenance phantom 102 and an arm 14 that carries the maintenance phantom 102. In addition, the PET device 400 is configured such that the arm 14 carries the maintenance phantom 102 to a measurement area 10a before acquisition of reference data by the data acquisition unit 20. The hangar 13 and the arm 14 are provided in a housing 10 of the PET device 400. In addition, the PET device 400 is configured such that the arm 14 stores the maintenance phantom 102 in the hangar 13 after acquisition of the reference data. The arm 14 and the phantom 102 are examples of a "carrying portion" and a "reference object to be measured" in claims, respectively. In addition, the PET device 400 is an example of the "nuclear medical diagnosis apparatus" in claims.

Specifically, a series of control operations from carrying of the maintenance phantom 102 to the measurement area 10a to storing of the maintenance phantom 102 in the hangar 13 can be fully automatically performed. The phantom 102 is injected with Ge-68, etc. whose half-life is comparatively longer than that of FDG. That is, the phantom 102 may not be frequently exchanged when compared to a case in which FDG, etc. is used. In FIG. 7, the hangar 13 and the arm 14 are schematically illustrated.

In this way, the maintenance phantom 102 may be automatically carried to the measurement area 10a and automatically stored in the hangar 13. As a result, it is possible to reduce a workload of the user involved in measurement of the maintenance phantom 102.

In addition, the PET device 400 may be configured such that the maintenance phantom 102 is carried by a carrying portion other than the arm 14. For example, the PET device 400 may be configured such that the maintenance phantom 102 is disposed on a lift type installation base and the maintenance phantom 102 is carried to the measurement area 10a by raising the installation base at the time of measurement. Further, the PET device 400 may be configured such that the maintenance phantom 102 is carried to the hanger 13 by lowering the installation base when measurement is completed.

For example, the first and second embodiments show an example in which the first area (the area A, the area A1, the area A2, and the area A3) and the second area (the area B, the area B1, the area B2, and the area B3) are continuous areas. However, the invention is not limited thereto. In the invention, the first area (the area A, the area A1, the area A2, and the area A3) and the second area (the area B, the area B1, the area B2, and the area B3) may correspond to the same area. In addition, the first area (the area A, the area A1, the area A2, and the area A3) and the second area (the area B, the area B1, the area B2, and the area B3) may partially overlap each other.

In addition, the first and second embodiments show an example in which the first area (the area A, the area A1, the area A2, and the area A3) and the second area (the area B, the area B1, the area B2, and the area B3) have substantially equal lengths. However, the invention is not limited thereto. In the invention, the first area (the area A, the area A1, the area A2, and the area A3) and the second area (the area B, the area B1, the area B2, and the area B3) may have different lengths.

In addition, the first embodiment shows an example in which each of the calibration data and the confirmation data corresponds to a part of the reference data. However, the invention is not limited thereto. In the invention, all the reference data may be designated and used as the calibration data and the confirmation data. Similarly, in the second embodiment, in each of the areas C1 to C3, all the normalization data may be designated and used as the calibration data and the confirmation data.

In addition, the first embodiment shows an example in which a time of transition from the first area (the area A) to the second area (the area B) corresponds to substantially a midpoint of a reference data acquisition time. However, the invention is not limited thereto. For example, the first area (the area A) may correspond to a beginning time of the reference data acquisition time. Similarly, in the second embodiment, the first areas (the areas A1 to A3) may correspond to beginning times of the areas C1 to C3, respectively.

In addition, the second embodiment shows an example in which the normalization unit 122 acquires the normalization data in three different areas C1 to C3. However, the invention is not limited thereto. For example, the normalization unit 122 may acquire the normalization data in two different areas or four different areas.

In addition, the second embodiment shows an example in which the three different areas C1 to C3 do not overlap each other. However, the invention is not limited thereto. For example, the areas C1 to C3 may partially overlap each other.

In addition, in the first and second embodiments, for the sake of convenience of description, a description has been given using a flow drive type flowchart in which processing of the controller is successively performed along a processing flow. However, the invention is not limited thereto. In the invention, a processing operation of the controller may be performed by event drive type (event driven type) processing that performs processing for each event. In this case, processing may be performed in a full event drive type or by combining event driving and flow driving.

The invention claimed is:

1. A nuclear medical diagnosis apparatus comprising:
   a plurality of detectors that detects annihilation radiation emitted from a reference object to be measured;
   a data acquisition unit that acquires reference data of the reference object to be measured based on a result of detecting, by the plurality of detectors, the annihilation radiation emitted from the reference object to be measured;
   a normalization unit that acquires a normalization factor for normalizing deviations of detection efficiencies among the plurality of detectors based on the reference data;
   a calibration unit that applies the normalization factor to at least a part of the reference data used for acquisition of the normalization factor to acquire a mutual calibration factor for calibrating a pixel value of a reconstructed image of the reference object to be measured to radioactive concentration of the reference object to be measured; and
   a quantitative value confirmation unit that compares radioactive concentration of the reference object to be measured calculated from a pixel value of an image of the reference object to be measured acquired by applying each of the normalization factor and the mutual calibration factor to at least a part of the reference data used for acquisition of the normalization factor with a quantitative value of the radioactive concentration of the reference object to be measured.

2. The nuclear medical diagnosis apparatus according to claim 1, wherein the data acquisition unit acquires the reference data by performing measurement once.

3. The nuclear medical diagnosis apparatus according to claim 1, wherein
   the calibration unit designates calibration data used for image reconstruction corresponding to a first area which is a part of the reference data and acquires the mutual calibration factor by applying the normalization factor to the calibration data to reconstruct the image, and
   the quantitative value confirmation unit designates confirmation data corresponding to a second area which is apart of the reference data and calculates radioactive concentration of the reference object to be measured by applying each of the normalization factor and the mutual calibration factor to the confirmation data.

4. The nuclear medical diagnosis apparatus according to claim 3, wherein the calibration unit is configured to designate pieces of calibration data corresponding to a plurality of different first areas in the reference data, respectively, to acquire a plurality of mutual calibration factors corresponding to the plurality of pieces of calibration data, respectively.

5. The nuclear medical diagnosis apparatus according to claim 3, wherein the quantitative value confirmation unit is configured to designate pieces of confirmation data corresponding to a plurality of different second areas in the reference data, respectively, to calculate radioactive concentrations of the reference object to be measured corresponding to the plurality of pieces of confirmation data, respectively.

6. The nuclear medical diagnosis apparatus according to claim 1, wherein the normalization unit is configured to determine that a normalization factor acquired this time is valid when a difference between the normalization factor acquired this time and a normalization factor acquired at a previous time is within a first ratio of the normalization factor acquired at the previous time, the calibration unit is configured to determine that a mutual calibration factor acquired this time is valid when a difference between the mutual calibration factor acquired this time and a mutual calibration factor acquired at a previous time is within a second ratio of the mutual calibration factor acquired at the previous time, and the quantitative value confirmation unit is configured to determine that radioactive concentration of the reference object to be measured calculated this time is valid when a difference between the calculated radioactive concentration of the reference object to be measured and a quantitative value of radioactive concentration of the reference object to be measured acquired in advance is within a third ratio of the quantitative value of the radioactive concentration of the reference object to be measured acquired in advance.

7. The nuclear medical diagnosis apparatus according to claim 6, wherein
   the normalization unit registers the normalization factor when it is determined that the normalization factor is valid,
   the calibration unit registers the mutual calibration factor when it is determined that the mutual calibration factor is valid, and
   the quantitative value confirmation unit registers the calculated radioactive concentration of the reference object to be measured when it is determined that the calculated radioactive concentration of the reference object to be measured is valid.

8. The nuclear medical diagnosis apparatus according to claim 1, further comprising:
   a hangar that stores the reference object to be measured for maintenance; and
   a carrying portion that carries the reference object to be measured for maintenance, wherein
   the carrying portion carries the reference object to be measured for maintenance to a measurement area before the reference data is acquired by the data acquisition unit and stores the reference object to be measured for maintenance in the hangar after the reference data is acquired.

9. A nuclear medical diagnosis apparatus comprising:
   a plurality of detectors that detects annihilation radiation emitted from a reference object to be measured; and
   a controller that acquires reference data of the reference object to be measured based on a result of detecting, by the plurality of detectors, the annihilation radiation emitted from the reference object to be measured, acquires a normalization factor for normalizing deviations of detection efficiencies among the plurality of detectors based on the reference data, acquires a mutual calibration factor for calibrating a pixel value of an image of the reference object to be measured acquired based on at least apart of the reference data used for acquisition of the normalization factor to radioactive concentration of the reference object to be measured, and compares radioactive concentration of the reference object to be measured calculated based on at least a part of the reference data used for acquisition of the normalization factor with a quantitative value of the radioactive concentration of the reference object to be measured.

10. A method for routine maintenance and inspection of a nuclear medical diagnosis apparatus, the method comprising:
   acquiring reference data of a reference object to be measured based on a result of detecting, by a plurality of detectors, annihilation radiation emitted from the reference object to be measured;
   acquiring a normalization factor for normalizing deviations of detection efficiencies among the plurality of detectors based on the reference data;
   applying the normalization factor to at least a part of the reference data used for acquisition of the normalization factor to acquire a mutual calibration factor for calibrating a pixel value of a reconstructed image of the reference object to be measured to radioactive concentration of the reference object to be measured; and
   comparing radioactive concentration of the reference object to be measured calculated from a pixel value of an image of the reference object to be measured acquired by applying each of the normalization factor and the mutual calibration factor to at least a part of the reference data used for acquisition of the normalization factor with a quantitative value of the radioactive concentration of the reference object to be measured.

* * * * *